(12) United States Patent
Cote et al.

(10) Patent No.: US 6,568,846 B1
(45) Date of Patent: May 27, 2003

(54) PULSED LASER HEATING SIMULATION OF THERMAL DAMAGE ON COATED SURFACE

(75) Inventors: Paul Cote, Clifton Park, NY (US); Gay Kendall, Troy, NY (US); Mark Todaro, Cohoes, NY (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/718,107

(22) Filed: Nov. 15, 2000

(51) Int. Cl.⁷ .............................................. G01N 21/00
(52) U.S. Cl. ............................. 374/5; 374/45; 374/46; 374/57
(58) Field of Search ................... 374/5, 134, 130, 374/131, 132, 45–46, 57

(56) References Cited

U.S. PATENT DOCUMENTS

| | | | | |
|---|---|---|---|---|
| 3,632,212 A | * | 1/1972 | Bernal | 73/355 |
| 4,475,027 A | * | 10/1984 | Pressley | 219/121 L |
| 4,819,658 A | * | 4/1989 | Kolodner | 374/120 |
| 4,965,451 A | * | 10/1990 | Solter | 250/330 |
| 4,999,499 A | * | 3/1991 | Bhatt | 250/342 |
| 5,052,816 A | * | 10/1991 | Nakamura et al. | 374/5 |
| 5,085,073 A | * | 2/1992 | Heyman et al. | 73/147 |
| 5,111,048 A | * | 5/1992 | Devitt et al. | 250/342 |
| 5,146,289 A | * | 9/1992 | Newman | 356/35.5 |
| 5,246,291 A | * | 9/1993 | Lebeau et al. | 374/5 |
| 5,308,161 A | * | 5/1994 | Stein | 374/5 |
| 5,417,494 A | * | 5/1995 | Kempa et al. | 374/5 |
| 5,562,345 A | * | 10/1996 | Heyman et al. | 374/5 |
| 5,803,606 A | * | 9/1998 | Petry et al. | 374/45 |
| 5,971,608 A | * | 10/1999 | Koizumi | 374/5 |
| 6,000,844 A | * | 12/1999 | Cramer et al. | 374/5 |
| 6,013,915 A | * | 1/2000 | Watkins | 250/341.1 |
| 6,396,635 B2 | * | 5/2002 | Kathman et al. | 359/599 |
| 2002/0018510 A1 | * | 2/2002 | Murphy et al. | 374/45 |
| 2002/0052621 A1 | * | 5/2002 | Fried et al. | 606/192 |

FOREIGN PATENT DOCUMENTS

| | | | | |
|---|---|---|---|---|
| EP | 1006346 A1 | * | 12/1998 | G01K/11/20 |
| JP | 0243574 | * | 12/1985 | 374/5 |

* cited by examiner

Primary Examiner—Diego Gutierrez
Assistant Examiner—Gail Verbitsky
(74) Attorney, Agent, or Firm—Michael C. Sachs; John F. Moran

(57) ABSTRACT

An apparatus and method for evaluating thermal barrier coating material on a surface of a part or component that is subjected to transient heat/thermal cycles. A pulsed laser heating apparatus that preferably uses lenses and optical fiber focusing components simulates conditions of brief heating on the test specimen. In the method of the invention, the temporal shape, spatial distribution, and total energy of the laser pulse are designed to produce a spot of uniform illumination and heat absorption on the test specimen that closely approximates the thermal loading that the specimen is expected to receive during use. The test specimen is then examined for thermally induced changes.

5 Claims, 3 Drawing Sheets

PULSED LASER HEATING SIMULATION OF THERMAL DAMAGE ON COATED SURFACE

STATEMENT OF GOVERNMENT INTEREST

The invention described herein may be manufactured and used by or for the United States Government for Governmental purposes without the payment of any royalties thereon.

BACKGROUND OF THE INVENTION

1. Field of the Invention

The invention pertains to an apparatus and method to simulate thermal loading of protective thermal barrier coatings to characterize thermal protection offered by such coatings that experience frequent, yet brief exposure periods of high-temperature and high-heat transfer conditions.

2. Description of the Prior Art

When large caliber guns are fired, their bores experience surface and subsurface damage caused by thermal effects, chemical attack by propellant gases, mechanical wear from projectile passage, and mechanical loading from gas pressurization. In particular, the internal surfaces of guns, (i.e. the bore, the face of the breech block and the primer vent if the gun uses a combustible cartridge case) suffer erosion from a number of sources. The passage of the hot gases from combustion of the primer and the main propellant at a high velocity causes considerable erosion of the primer vent, internal face of the breech block and the gun bores. The passage of the projectile along the barrel, its driving band engaging with the rifling grooves causes further erosion of the bore, which is enhanced by the escape of gases around the trailing edge of the driving band. The erosion results in the formation of pits in the bore and wearing away of accurately machined parts of the gun, such as the firing mechanism and rifling grooves. This is especially pronounced in sections that have been subjected to electro-chemical corrosion resulting from deposition of pyrolysis products such as sulfides, nitrates and sulfates in small cracks in the gun from which they are not easily removed by cleaning. In addition, driving band debris builds up on the rifling grooves. This results in degradation of gun performance. The reclamation of gun components is a difficult and costly process, thus it is desirable to limit surface erosion if possible.

In particular, gun bore surfaces are typically subjected to short (5 to 10 millisecond) pulses of high thermal energy during firing of a munitions round. Included among the deleterious thermal effects resulting from exposure to these high thermal energy pulses are melting, phase transformations, and surface cracking (heat checking).

Although heating components and materials in a furnace can provide some information about the potential of a coating to protect a substrate, the slow, uniform heating typical of furnaces is quite different from the intense, yet brief, thermal conditions for which thermally protective coatings are most useful. For example, such a technique of using continuous accelerated heating with associated corrosion and erosion of the test specimen is taught in U.S. Pat. No. 5,793,042. Moreover, heating in a furnace does not solve the problem of duplicating the expected thermal environment and characterizing how the coating and substrate system behaves in transient-type environments, an essential condition of the test method of the present invention.

Known test apparatus that can simulate brief intense pulsed energy events include a "vented combustor" that can simulate, on a small scale, many of the actual conditions present in a large caliber gun during firing. In this device, a propellant charge is ignited in a confined space and at the appropriate time allowed to flow through an orifice, potentially exposing a test area to temperatures, pressures, and reaction products similar to those seen within a large caliber gun during firing. However, this method uses combustible, energetic agents and requires that utmost safety precautions be observed to prevent hazard and injury to personnel and test equipment before, during and after such test.

Although a vented combustor can come much closer than a furnace to reproducing the desired thermal conditions, this device is unsatisfactory in several ways. First, because of the complicated interaction of the several variables involved in using a vented combustor, it is difficult, and not necessarily possible, to ensure that it is adequately reproducing the desired heat transfer at the specimen surface. Second, using a vented combustor, one cannot isolate purely thermal effects from chemical and mechanical effects. Finally, and most critically, a vented combustor is grossly inconvenient and expensive device to operate. Special facilities and trained personnel are required for handling propellant and operating the device, making it a very expensive mode of testing.

The aforementioned prior art systems and methods do not afford the needed experimental controls for efficient, safe and time-accelerated testing of thermal protective barrier coatings, which the present invention resolves. Thus, the present invention provides a means for testing and evaluating capabilities of thermal barrier coatings on internal gun components that encounter brief high-energy conditions during gun firing.

SUMMARY AND ADVANTAGES OF THE INVENTION

The invention pertains to an apparatus and method for evaluating thermal barrier coating material on a surface of a part or component that is subjected to transient heat/thermal cycles. A pulsed laser heating apparatus that preferably includes lenses and optical fiber components produces conditions of brief heating on the test specimen.

In the method of the invention, the temporal shape, spatial distribution, and total energy of the laser pulse are designed to produce a spot of uniform illumination and heat absorption on the test specimen that closely approximates the thermal loading that the specimen is expected to receive during use. The test specimen is then examined for thermally induced changes.

Thermally protective barrier coatings are often useful when rapid and intense heating occurs at the surface of a component for brief periods of time (less than ten milliseconds, for example). In such applications, various coatings can reduce the peak temperature in the underlying material and thus extend its service life. Although the preferred use of the invention has been for testing TBC chromium coatings that are electrodeposited onto a high-strength steel alloy, where the application of such a coating is large caliber guns, the invention is nevertheless applicable to a broad range of other coatings and substrates, including ceramic and composite coatings where transient high-temperature conditions occur as well. Pulsed laser heating provides an easily controllable way to heat a coating and substrate system in a manner that can closely approximate the intense, yet brief, heating conditions for which thermally protective coatings are often useful.

Accordingly, advantages of the present invention include providing a testing laser heating apparatus and method that:

a) allows heat input to the test specimen and the duration of the heating pulse to be easily measured and easily controlled;

b) allows for pulsed laser heating that heats in a manner largely free from the interference of chemical and mechanical effects, thus isolating thermal effects from chemical and mechanical effects; and c) effectuates material testing of transient heating on a test specimen that is much simpler, safer, and less expensive to operate.

Still further advantages will become apparent from consideration of the ensuing detailed description.

DETAILED DESCRIPTION OF THE PREFERRED EMBODIMENT

Experiments with pulsed laser heating can characterize the effects of thermal shock loading on gun bores and distinguish their effects from the other factors that contribute to bore damage. Pulsed laser heating can conveniently provide information on the evolution of coating degradation with number of pulses and pulse energy, corresponding to number of rounds and propellant flame temperature. This method allows comprehensive study of erosion phenomena while avoiding the high costs of actual firing of large caliber guns. Upon use, this method could reduce costs for and accelerate the development of improved erosion-resistant thermal barrier coatings for use in guns and other components that operate under repetitive high-energy conditions. Such a testing protocol can be extrapolated for use in testing other components that experience transient high-energy heating pulses, analogous to a gun firing event.

Figure 1:
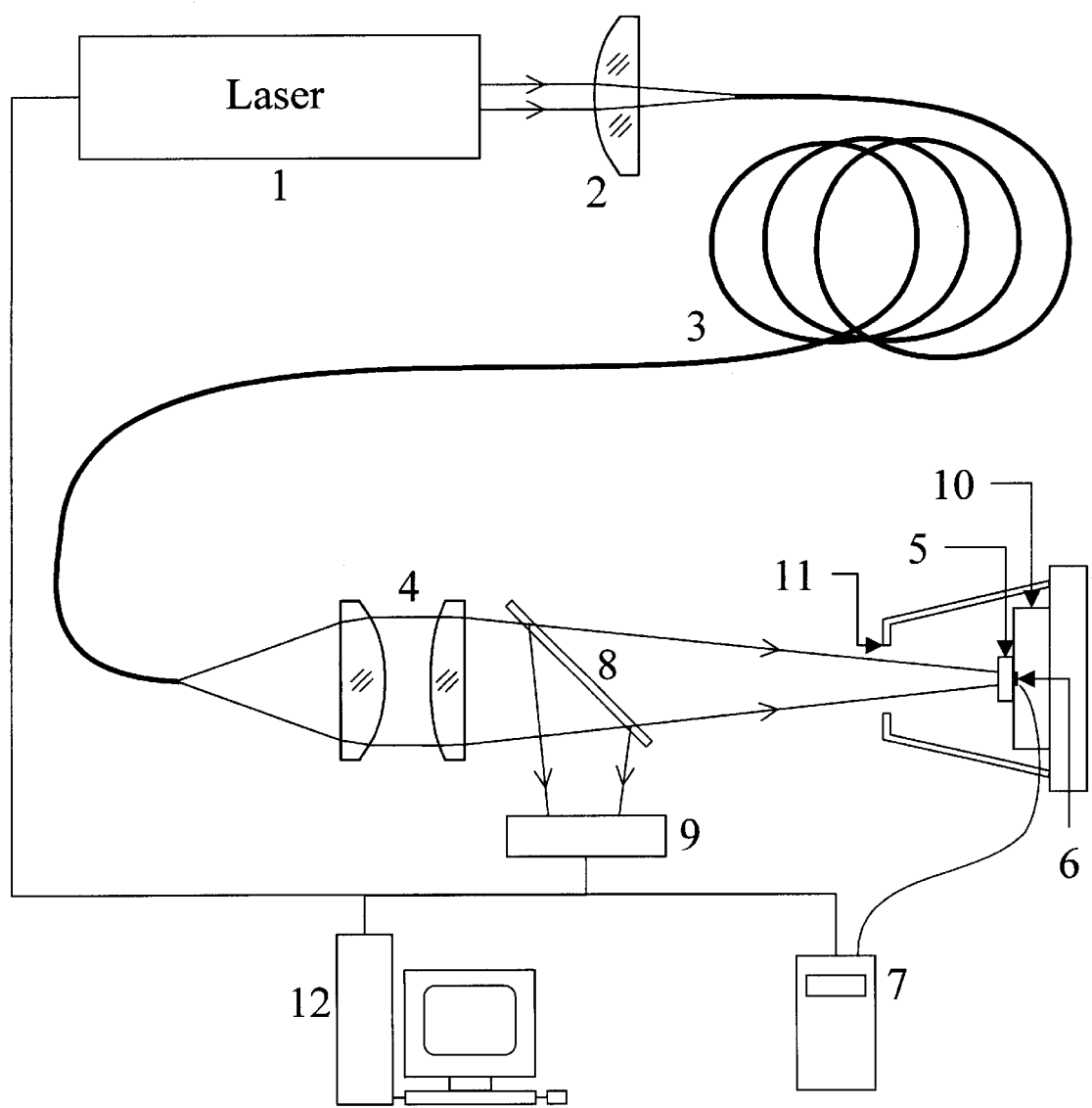
FIG. 1 shows an exemplary form of the apparatus of the invention using pulsed laser heating to simulate transient heating of a test specimen.

FIG. 1 shows in exemplary form, pulses of radiation from a laser (1), preferably a neodymium-doped yttrium aluminum garnet (Nd:YAG) laser, are delivered to the test specimen surface with a uniform energy distribution at that surface. A lens assembly (2) focuses the light from the laser into an optical fiber (3), preferably an all-silica optical fiber having a core diameter of 600 micrometers, cladding diameter of 720 micrometers, and numerical aperture of 0.20. The optical fiber provides ease of use during testing and provides an improved uniform distribution of energy at the surface of the test specimen. Preferably a lens assembly (4) is used at the output of the fiber to focus and form a magnified image of the end face of the optical fiber onto the surface of the test specimen (5). Thus, the cross-sectional distribution of energy at the surface of the test specimen is substantially uniform over a circular spot with a diameter that depends upon the diameter of the optical fiber core and the magnification of the output optics. The radiation from a Nd:YAG laser usually has a wavelength of approximately 1.064 micrometers and can be pulsed with a duration of 5 milliseconds (FWHM). The spot diameter using the above components at the specimen surface can be approximately 2.6 millimeters. In testing thermal barrier coatings (TBC) for gun bores, these parameters ensure adequate simulation conditions since typical TBC coating thickness is approximately 0.1 mm, giving a spot diameter to coating thickness ratio of 26, so that a large central portion of the spot approximates the bore surface.

For many protective thermal barrier coatings, a significant portion of the laser energy is reflected rather than absorbed. Normally it is not know beforehand what portion will be reflected and what portion absorbed. If comparisons and predictions are to be made using pulsed laser heating, one must measure, for each pulse, the amount of laser energy that is actually absorbed by the specimen rather than that which is merely incident upon it. This quantitative measure of absorbed energy is achieved calorimetrically. Typically a test specimen is about 3 millimeters thick and cut to a square 6 millimeters on edge. A temperature sensor (6) with appropriate display unit (7) or oscilloscope is used to measure the net temperature rise of the bulk specimen. The sensor (6) can be a thermocouple that is mechanically adhered to the back surface of the specimen (5). The laser heating apparatus shown in FIG. 1 is incorporated with a test stand fixture on which an end of the optical fiber (3) is mounted and which includes the output lens assembly (4), a beam splitter (8) to direct a portion of the energy to a laser energy meter (9), and an insulated specimen holder (10) with appropriate physical positioning mechanisms for proper focusing of the laser beam on the test specimen. A shroud (11), typically an inverted 8-ounce disposable cup with the bottom cut out, can be used to reduce air-flow near the test specimen to assure repeatability and accuracy of the calorimetric measurement of test specimen energy absorption.

Alternative components for the above listed are as follows: The laser (1) can be a carbon dioxide laser, the use of which would, however, require modification or elimination of other optical components, including the optical fiber. Another form of the temperature sensor (6) can be a remote infrared thermal sensor calibrated for determining temperature of the test specimen. Control of the laser (1) and measurements from the temperature sensor (6) and laser energy meter (9) can be automated using a computer (12) with appropriate software for maintaining accurate control of testing conditions and data acquisition during test.

Figure 2:
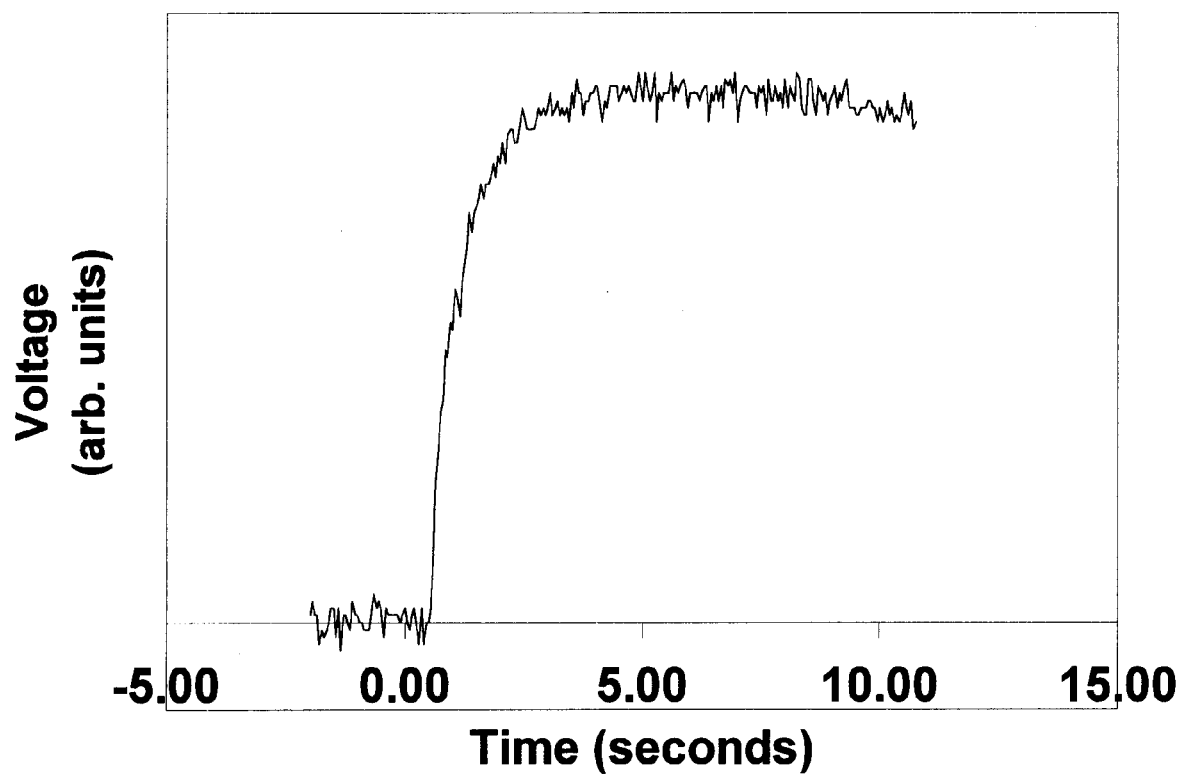
FIG. 2 shows a plot of thermocouple voltage versus time after pulsed laser heating for a thermocouple that is adhered to a back surface of the test specimen.

FIG. 2 shows an exemplary plot of the temperature sensor (6) output after pulsed laser heating. In this case, the plotted quantity is the voltage from a thermocouple adhered to the back surface of the test specimen. The temperature reaches a maximum soon after pulsing and does not decay significantly for several more seconds. A digital thermocouple readout device can be used for finding the maximum temperature rise for the test specimen. The energy absorbed can then be estimated by multiplying that temperature rise by the heat capacity of the test specimen.

When examining a test specimen, the method of the invention includes the following steps:

(1) The following are assumed to be known for a test specimen: (a) the duration of the heating event to be simulated, (b) the desired energy density (energy per unit area absorbed during the heating event to be simulated), and (c) the heat capacity of the test specimen.

(2) Next, a laser is adjusted to deliver a pulse of duration equal to the duration of the heating event to be simulated and energy E that equals $IS/\alpha$, where I is the desired energy density, S is the area of the illuminated spot on the specimen, and α is an estimate of the fraction of incident energy expected to be absorbed by the specimen. This energy distribution is designed to be nearly uniform in cross-section incident as a spot on the test specimen, a critical feature so as to model actual use thereof, e.g. a surface of a gun bore during firing.

(3) The test specimen is then heated by one pulse of the laser, the maximum temperature measured, the absorbed energy determined by multiplying the temperature rise by the heat capacity of the specimen, and the absorbed energy density determined by dividing the absorbed energy by the area of the illuminated spot on the specimen.

(4) If the absorbed energy density agrees sufficiently with the desired energy density, then steps (2) and (3) are repeated as many times as desired, revising a as necessary. If after any laser pulse the absorbed energy density does not agree sufficiently with the desired energy density, then steps (2) through (3) are repeated on a fresh spot on the specimen or a new specimen as many times as desired using revised estimates of a where necessary.

(5) After a specimen is successfully pulsed for the desired number of cycles at the desired energy density, the specimen is prepared for examination by cutting to expose a cross section of the illuminated area, mounting, polishing and etching as required for viewing purposes, and examined with a microscope to determine the effects of heating.

Example of Pulsed Laser Heating Simulation

Since World War-II, gun bore surfaces have included chromium coatings to protect the bores of large caliber gun barrels from harsh thermal (as well as mechanical and chemical) conditions. To date, this practice is continued wherein such surfaces are often electroplated with high-contractile (HC) chromium to enhance resistance to erosion. (The terms high-contractile and low-contractile refer to the tendency of chromium electrodeposits to shrink upon annealing by various amounts depending on plating conditions.) Higher performance requirements have led to efforts to obtain higher erosion resistance than that of HC chromium. Low contractile (LC) chromium electroplated coatings were recently developed in order to exploit benefits of bore coatings with lower microcrack densities. Current efforts are also under way in developing refractory metal bore surface coatings (such as magnetron sputtered tantalum).

Assuming that coating composition is selected for appropriate resistance to melting and chemical attack, the important characteristics of bore protective coatings are good adhesion and resistance to cracking during thermal shock loading. Cracking provides pathways through the coating for chemical attack of the vulnerable underlying steel by the chemically aggressive propellant gas. There is extensive documentation of the experience with various gun bore protective coatings including HC and LC chromium. See (a) Burlew, J. S., ed. "Hypervelocity Guns and the Control of Gun Erosion," Summary Technical Report of the National Defense Research Committee, Division 1, Office of Scientific Research and Development, Washington, D.C., 1946; (b) Ahmad, I., "The Problem of Gun Barrel Erosion-An Overview," *Gun Propulsion Technology*, (L. Steifel, ed.), Progress in Astronautics and Aeronautics Series, AIAA, Washington D.C., 1988, pp. 311–355; and (c) *Proceedings of the Sagamore Workshop on Gun Barrel Wear and Erosion,* Wilmington, Del., Jul. 29–31, 1996, (R. J. Dowding, J. S. Montgomery, U.S. Army Research Laboratory, eds.). In particular, the more informative compilation of this experience is the 1946 National Defense Research Committee Report "Hypervelocity Guns and the Control of Gun Erosion".

It has been observed that HC chromium is significantly more cracked than LC chromium after firing, suggesting that the difference in HC and LC contraction upon annealing is responsible for this difference in crack density. However, an alternative explanation may be that HC chromium is more susceptible to mechanical damage from projectile passage than LC chromium. A related question is whether the time at high temperature during firing is sufficient to permit the chrome contraction process to proceed. The contraction process in these metastable systems is still poorly understood. If contraction is not a factor and the observed cracking results primarily from the thermal shock process in the brittle HC and LC chromium, then HC and LC chromium should exhibit similar crack features.

Figure 3:
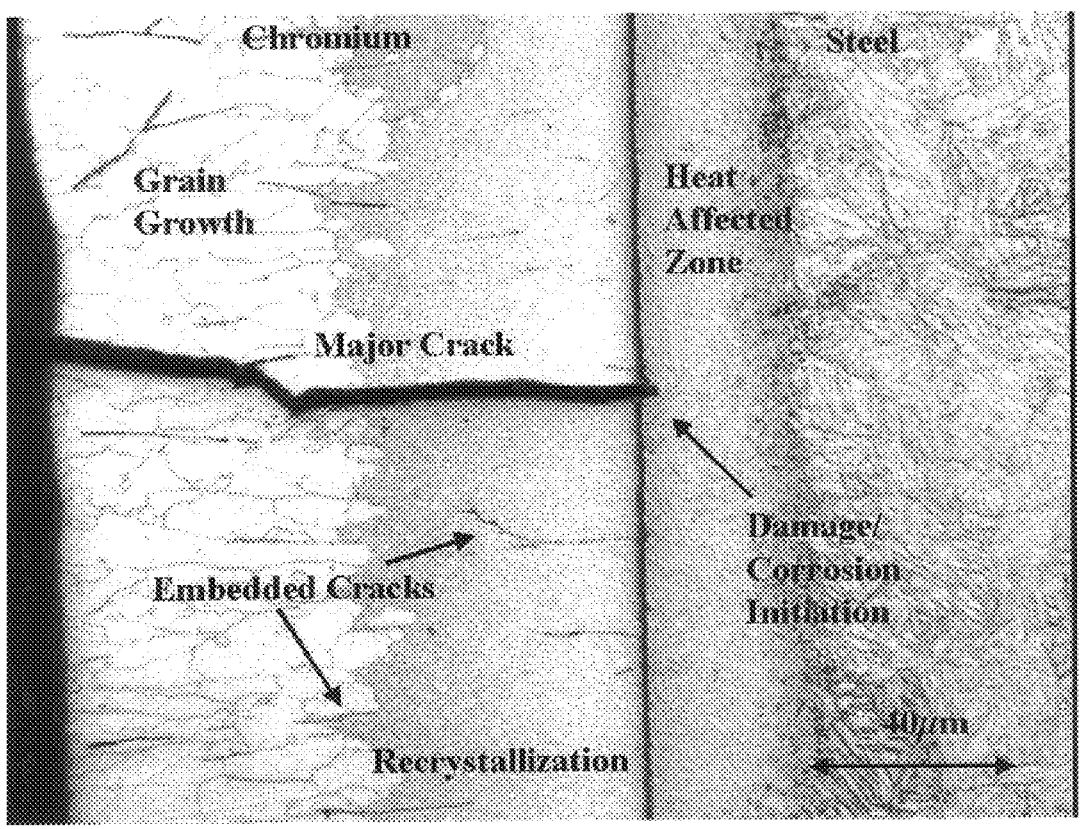
FIG. 3 shows a laser-scanning confocal microscope image of a pulsed-laser-heated electrodeposited HC chromium on gun steel test specimen using the invention. In the drawings and constituted as such, like numerals indicate like parts.

Pulsed laser heating, using the apparatus shown in FIG. 1, was applied in the present study to address such issues. FIG. 3 shows a photograph of a cross-section of a test piece using the method of the invention, showing an electrodeposited HC-chromium on steel substrate after being subjected to 20 laser pulses at incident energy of 3 J/mm$^2$. The specimen was given a hydrogen anneal prior to laser pulsing. As shown, features of a simulated heavily gun-fired chromium plated gun bore section are present, which include thermal quench cracking, grain growth of chromium, recrystallization of chromium, the formation of a heat-affected zone in the substrate steel, and even chemical attack (oxidation) of the steel at the base of chromium cracks.

Results from pulsed laser heating of HC chromium indicated that thermal shock cracking in the laser heated area develops by enlargement of the preexisting cracks that were generated in the specimen during the deposition and the subsequent anneal to remove hydrogen. The preexisting cracks are visible in the region surrounding the area heated by laser pulsing. Equivalent laser pulsing of LC chromium showed that, in contrast to the HC case, there were no preexisting cracks in the coating as evident from the absence of cracks in the region surrounding the laser pulsed area. The thermal shock cracking in this case represents initiation and growth of cracks. The crack density and crack widths are both smaller in the LC chromium coating.

Use of the invention has included testing of sputtered tantalum on a substrate as a test specimen, which potentially may be an improved thermal barrier material that replaces chromium coatings in gun bores. One potential problem with this thermal protective coating design is frequent occurrence of the hard, brittle, metastable beta phase in the deposit. Highly brittle coatings inherently exhibit low thermal shock resistance. The origin of the beta phase in sputtered deposits is unknown. Another potential problem with sputtered coatings is the possible deposition of a porous, columnar morphology, commonly referred to as Zone 1 deposition, as discussed in Thorton, J., Ann. Rev. Mater. Sci. 1977, 7:239–60. The porosity tends to form between the columns, which produces a weak coating that may be highly susceptible to thermal shock cracking. Pulsed laser heating was applied to assess the relative thermal shock resistance of sputtered alpha and beta phases and coatings deposited under Zone 1 conditions. The beta phase coating cracked as a result of the thermal shock from one laser pulse with incident energy of 1.3 J/mm$^2$. No cracking is observed in the alpha phase following identical pulsing, indicating good resistance to thermal shock. The use of the invention saved much time and money for such evaluation of materials, and provides an illustrative use of the invention. In conclusion, the present invention offers new insights into a variety of issues relating to gun bore coating degradation as a result of severe thermal cycling, and thus serve to illustrate the broad range of problem areas relating to bore protective coatings that can be investigated using a pulsed laser heating method.

Although the preferred use of the apparatus and method of the invention is testing of specified material systems on a substrate of interest as related to gun technologies, it can also be used in other applications where layered or unlayered coatings are exposed to transient high-energy events such as automotive engines, diesel engines and gas turbines. Indeed, the invention is broadly applicable to test specimens representative of protective thermal barrier coating systems that are typically applied on superalloy substrates and include an inner bondcoat on the substrate, an outer thermal insulating layer located thereon, which typically includes more ceramic materials, and a thin intermediate ceramic layer located between the bondcoat and the thermally insulating layer to promote adherence of the thermally insulating layer.

There are a variety of TBC coating systems currently available which reduce attack on the component material by aggressive reactive species such as oxygen, sulfur, carbon, nitrogen, halogens, or sodium and/or which reduce corrosive damage resulting from exposure to high temperatures. One of the simplest forms of protective coating is an oxide scale, which naturally forms on many metal alloys as a result of exposure to air or other oxidizing media, especially at high temperatures. A scale such as chromium oxide, aluminum oxide, or silicon oxide isolates the bare alloy from the environment and thereby slows down further corrosive attack. Other known coatings include those based on aluminium, particularly a simple aluminide applied by an aluminizing process, a modified aluminide in which the aluminium is combined with another element such as chromium, platinum, or palladium, or a more complex metal overlay coating of the general formula $MCrAl_y$, where M is another metallic element. Protective coatings based on ceramic materials have also been developed, based particularly on zirconia. These latter coatings are useful in high temperature applications and form a part of the known thermal barrier coatings which consist of an MCrAly underlay or "bond" coat and a zirconia overlay. In such TBC coating systems, spallation of the outer thermal insulating layer can occur at the intermediate layer as a result of residual compressive stresses in the TBC system, especially between the bond coat and intermediate layer. The invention can be used to examine this condition when components using TBC are exposed to transient high-energy events.

Thus, many modifications and variations of the present invention are possible in view of the above disclosure. Therefore to be understood, that within the scope of the appended claims, the invention may be practiced otherwise than as specifically described.

What is claimed is:

1. A method for testing thermal barrier coating material for suitability in a large caliber gun by thermally simulating the transient extreme temperature effects on such material of repeated firing of the gun, on a test specimen of such thermal barrier coating material, said test specimen comprising at least one layered material deposited on a substrate, the method for evaluating the test specimen comprising the steps of:
   a) providing a model of expected energy absorption of the specimen during the event which includes: i) a duration of the heating event to be simulated, ii) an energy per unit area absorbed during the simulated heating event, and iii) a heat capacity of the test specimen;
   b) irradiating the test specimen to provide an area of uniform heating having a temporal shape and energy absorption that closely approximates thermal loading that the specimen receives during actual use;
   c) measuring energy absorbed by the test specimen; and
   d) examining the test specimen.

2. A method for testing thermal barrier coating material for suitability in a large caliber gun by thermally simulating the transient extreme temperature effects on such material of repeated firing of the gun, on a test specimen of such thermal barrier coating material, said test specimen comprising at least one layered material deposited on a substrate, the method for evaluating the test specimen comprising the steps of:
   a) providing a model of expected energy absorption of the specimen during the event;
   b) irradiating the test specimen to provide an area of uniform heating having a temporal shape and energy absorption that closely approximates thermal loading that the specimen receives during actual use; including the further steps of: adjusting the laser to deliver a pulse of duration equal to duration of the heating event to be simulated and of energy E that equals $IS/\alpha$, where I is desired energy density, S is area of an illuminated spot on the test specimen, and $\alpha$ is an estimate of fractional incident energy expected to be absorbed by the specimen, and providing an energy distribution that is nearly uniform on the test specimen, thereby modeling actual use of the test specimen;
   c) measuring energy absorbed by the test specimen; and
   d) examining the test specimen.

3. A method for testing thermal barrier coating material for suitability in a large caliber gun by thermally simulating the transient extreme temperature effects on such material of repeated firing of the gun, on a test specimen of such thermal barrier coating material, said test specimen comprising at least one layered material deposited on a substrate, the method for evaluating the test specimen comprising the steps of:
   a) providing a model of expected energy absorption of the specimen during the event;
   b) irradiating the test specimen to provide an area of uniform heating having a temporal shape and energy absorption that closely approximates thermal loading that the specimen receives during actual use;
   c) measuring energy absorbed by the test specimen; and
   d) examining the test specimen, including the further steps of: cutting the specimen to expose a cross section of the illuminated area, mounting, preparing a cross-sectional surface, and examining the specimen with a microscope to determine simulated heating effects.

4. A method for destructive testing thermal barrier coating material for suitability in a large caliber gun by thermally simulating the transient extreme temperature effects on such material of repeated firing of the gun, on a test specimen of such thermal barrier coating material representative of an internal gun bore surface, said test specimen comprising at least one layered material deposited on a substrate, the method for evaluating the test specimen comprising the steps of:
   a) providing a model of expected energy absorption of the specimen during the event;

b) irradiating the test specimen to provide an area of uniform heating having a temporal shape and energy absorption that closely approximates thermal loading that the specimen receives during actual use;

c) measuring energy absorbed by the test specimen; and d) examining the test specimen.

5. A method for destructive evaluation of thermal barrier coating material for suitability in a large caliber gun by thermally simulating the transient extreme temperature effects on such material of repeated firing of the gun, on a test specimen of such thermal barrier coating material, said test specimen comprising at least one layered material deposited on a substrate, the method for evaluating the test specimen comprising the steps of:

a) providing a model of expected energy absorption of the specimen during the event;

b) irradiating the test specimen to provide an area of uniform heating having a temporal shape and energy absorption that closely approximates thermal loading that the specimen receives during actual use;

c) measuring energy absorbed by the test specimen; and d) examining the test specimen.

* * * * *